United States Patent
Golightly

(10) Patent No.: US 6,248,575 B1
(45) Date of Patent: Jun. 19, 2001

(54) NUCLEIC ACIDS ENCODING POLYPEPTIDES HAVING L-AMINO ACID OXIDASE ACTIVITY

(75) Inventor: Elizabeth J. Golightly, Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/314,242

(22) Filed: May 18, 1999

Related U.S. Application Data

(63) Continuation-in-part of application No. 09/080,428, filed on May 18, 1998, now abandoned.

(51) Int. Cl.[7] ............... C12N 9/02; C12N 9/06; C12N 1/20; C12N 15/00; C07H 21/04
(52) U.S. Cl. ............ 435/189; 435/191; 435/252.3; 435/320.1; 536/23.2
(58) Field of Search .................... 435/189, 191, 435/252.3, 320.1, 440; 536/23.2

(56) References Cited

U.S. PATENT DOCUMENTS 5,536,655 * 7/1996 Thomas et al. .................. 435/209
5,801,035 * 9/1998 Schneider et al. ............... 435/189
5,817,499 * 10/1998 Dalboge et al. .................. 435/200

FOREIGN PATENT DOCUMENTS 55-43409   3/1990  (JP) .
94/25574  11/1994  (WO) .

OTHER PUBLICATIONS

Niedermann and Lerch, 1990, Journal of biological Chemistry 265: 17246–17251.

Bockholt et al., 1995, Biochimica et Biophysica Acta 1264: 289–293.

* cited by examiner

*Primary Examiner*—Elizabeth Slobodyansky
(74) *Attorney, Agent, or Firm*—Robert L. Starnes

(57) ABSTRACT

The present invention relates to isolated nucleic acid sequences encoding polypeptides having L-amino acid oxidase activity. The invention also relates to nucleic acid constructs, vectors, and host cells comprising the nucleic acid sequences as well as recombinant methods for producing the polypeptides.

10 Claims, 5 Drawing Sheets

```
ATGGACAATGTTGACTTTGCTGAATCTGTCCGAACCCGCTGGGCGAGGCGACTTATTCGTGAGAAGGTCG    70
 M  D  N  V  D  F  A  E  S  V  R  T  R  W  A  R  R  L  I  R  E  K  V
CCAAGGAACTCAACATTCTAACGGAAAGACTTGGTGAGGTGCCGGAATCCCTCCTCCAAACGAAGGCAG   140
 A  K  E  L  N  I  L  T  E  R  L  G  E  V  P  G  I  P  P  P  N  E  G  R
ATTCCTGGGCGGGCTACTCTCACGACAATCTACCATCTGATCCTCTATTCCAGCATTAAGCCGGCT     210
 F  L  G  G  G  Y  S  H  D  N  L  P  S  D  P  L  Y  S  S  I  K  P  A
CTTCTAAAGGAGGCTCCTCGAGCAGAAGAGGAACTGCCGCCTCGAAAGGTGTGCATTGTAGGCGTGGTG   280
 L  L  K  E  A  P  R  A  E  E  E  L  P  P  R  K  V  C  I  V  G  A  G
TTTCCGGCCTCTACATAGCCATGATTTTGGACGATTTGAAAATCCCAAATCTCACTTACGACATCTTTGA  350
 V  S  G  L  Y  I  A  M  I  L  D  D  L  K  I  P  N  L  T  Y  D  I  F  E
ATCCAGTTCCAGAACTGGCGGTGCCCTGTATACGACGCCACCACTTCACCGACGCCAAGCATGACTATTACGAC 420
 S  S  S  R  T  G  G  R  L  Y  T  H  H  F  T  D  A  K  H  D  Y  D
ATTGGTGCTATGCGATACCCTGACATCCCCAGCATGAAACGAACCTTTAACCTGTTTAAACGTACTAAGA   490
 I  G  A  M  R  Y  P  D  I  P  S  M  K  R  T  F  N  L  F  K  R  T  K
TGCCCCTCATCAAGTATTACCTTGATGGCGAGAATACCCCTCAGCTGTACAATAACCACTTCTTCGCCAA  560
 M  P  L  I  K  Y  Y  L  D  G  E  N  T  P  Q  L  Y  N  N  H  F  A  K
GGGTGTGTCGGACCCCTATATGGTGAGCGTGGCCAATGGCGGCCACCGTGCCAGACGATGTTGTCGACAGT 630
 G  V  S  D  P  Y  M  V  S  V  A  N  G  G  T  V  P  D  D  V  V  D  S
GTTGGAGAGAAGTTACAGCAGGCTTTCGGTTATTACAAAGAGAAGCTTGCTGAGGACTTCGACAAAGGT   700
 V  G  E  K  L  Q  Q  A  F  G  Y  Y  K  E  K  L  A  E  D  F  D  K  G
TCGATGAGCTCATGCTCGTCGTAGACGACATGACTACTCGAGAGTACTTGAAGCGAGGCGGACCCAAGGGAGA  770
 F  D  E  L  M  L  V  D  D  M  T  T  R  E  Y  L  K  R  G  G  P  K  G  E
GGCGCCCAAGTATGACTTCTTCCGCCATCCAATGGAGAGACACAAAACACCGGGACGAACTTGTTTGAT   840
 A  P  K  Y  D  F  F  A  I  Q  W  M  E  T  Q  N  T  G  T  N  L  F  D
CAGGCCGTTTCTGAAAGCGTCATTGACTGCGTTTGACTTTGACTTTGACTTTGACAACCCGAATGGTACTGCA   910
 Q  A  F  S  E  S  V  I  D  S  F  D  F  D  N  P  T  K  P  E  W  Y  C
TCGAGGGAGGAACATCGCTTTTGGTGGACGCCATGGAGAAAAACCCTTGTCCACAAGTACAGAACAACAA   980
 I  E  G  T  S  L  L  V  D  A  M  E  K  T  L  V  H  K  V  Q  N  N  K
GAGAGTTGATGCCGATATAGCACACCGTCTTCAACACCTTGGACGCTCCAGATGATGCAACATGTCGGTCAGGATAGGCGGA  1050
 R  V  D  A  I  S  I  D  L  D  A  P  D  D  G  N  M  S  V  R  I  G  G
AAGGAACACTCCGGATATAGCACACCGTCTTCAACACCGTCTTGGGCGTGCCTTGACCGCATGGATCTGC  1120
 K  E  H  S  G  Y  S  T  V  F  N  T  T  A  L  G  C  L  D  R  M  D  L
```

Fig. 4A

```
GTGGTCTCAACTTGCACCCTACGCAAGCGGATGCCATTCGATGTTTGCATTATGACAACTCGACAAAGGT  1190
 R  G  L  N  L  H  P  T  Q  A  D  A  I  R  C  L  H  Y  D  N  S  T  K  V
AGCTCTCAAGTTTAGCTACCCGTGGTGGATCAAGGACTGTGGCATCACTTGCGGTGGCGCCCTCGACT    1260
 A  L  K  F  S  Y  P  W  W  I  K  D  C  G  I  T  C  G  G  A  A  S  T
GATCTGCCCTCTACGAACTTGGCTGTCTCAGGACGCAACTCGCATTGGATCGTTGGTGAAGGAAGCTCCACAGCCGCC  1400
 D  L  P  L  R  T  C  V  Y  P  S  Y  N  L  A  D  T  G  E  A  V  L  L
CCTCATACACTTGGTCTCAGGACGCAACTCGCATTGGATCGTTGGTGAAGGAAGCTCCACAGCCGCC    1400
 A  S  Y  T  W  S  Q  D  A  T  R  I  G  S  L  V  K  E  A  P  P  Q  P  P
CAAGGAAGATGAGCTCGTCGAGCTGATCCTGCAGAACCTGGCCCGCCTGAGCACGCATATGACTTAT   1470
 K  E  D  E  L  V  E  L  I  L  Q  N  L  A  R  L  H  A  E  H  M  T  Y
GAGAAGATTAAGGAGGCTTACACGGGCGTATATCACGCTGGGCTAATGATCCCAATGTCGGTG       1540
 E  K  I  K  E  A  Y  T  G  V  Y  H  A  Y  C  W  A  N  D  P  N  V  G
GCGCTTTCGCCCCTCTTCGGTCCCGGCCAATCTGTATCCGTACCTGATGCGACCAGCGGCGGG       1610
 A  F  A  L  F  G  P  G  Q  F  S  N  L  Y  P  Y  L  M  R  P  A  A  G
CGGCAAGTTCCATATCGTCGGAGAGCCATCTAGCGTACATCCTGATCATAGGGTCTTTGGAGAGT     1680
 G  K  F  H  I  V  G  E  A  S  S  V  H  H  A  W  I  I  G  S  L  E  S
GCTTACACCGCTGTTTACCAGTTCCGATACAAGATGTGGGATTACTTAAAGCTGTTGTTGGAGC      1750
 A  Y  T  A  V  Y  Q  F  R  Y  K  M  W  D  Y  L  K  L  L  E
GCTGGCAGTATGGTCTCCAGGAGTACCAGGTGAAGATCTAA 1854
 R  W  Q  Y  G  L  Q  E  L  E  T  G  K  H  G  T  A  H  L  Q  F  I  L  G
TTCACTTCCCAAGGAGTACCAGGTGAAGATCTAA 1854
 S  L  P  K  E  Y  Q  V  K  I
```

Fig. 4B

```
                              SEQUENCE LISTING

<160> NUMBER OF SEQ ID NOS: 12

<210> SEQ ID NO: 1
<211> LENGTH: 1854
<212> TYPE: DNA
<213> ORGANISM: Trichoderma harzianum

<400> SEQUENCE: 1
atggacaatg ttgactttgc tgaatctgtc cgaacccgct gggcgaggcg acttattcgt      60
gagaaggtcg ccaaggaact caacattcta acggaaagac ttggtgaggt gcccggaatc     120
cctcctccaa acgaaggcag attcctgggc ggcggctact ctcacgacaa tctaccatct     180
gatcctctct attccagcat taagccggct cttctaaagg aggctcctcg agcagaagag     240
gaactgccgc ctcgaaaggt gtgcattgta ggcgctggtg tttccggcct ctacatagcc     300
atgattttgg acgatttgaa aatcccaaat ctcacttacg acatctttga atccagttcc     360
agaactggcg gtcgcctgta tacgcaccac ttcaccgacg ccaagcatga ctattacgac     420
attggtgcta tgcgataccc tgacatcccc agcatgaaac gaacctttaa cctgtttaaa     480
cgtactaaga tgcccctcat caagtattac cttgatggcg agaataccec tcagctgtac     540 aataaccact tcttcgccaa gggtgtgtcg gaccctata tggtgagcgt ggccaatggc     600
ggcaccgtgc cagacgatgt tgtcgacagt gttggagaga agttacagca ggctttcggt     660
tattacaaag agaagcttgc tgaggacttc gacaaagggt tcgatgagct catgctcgtc     720
gacgacatga ctactcgaga gtacttgaag cgaggcggac ccaagggaga ggcgcccaag     780
tatgacttct tcgccatcca atggatggag acacaaaaca ccgggacgaa cttgtttgat     840
caggcgtttt ctgaaagcgt cattgactcg tttgactttg acaacccgac aaaacccgaa     900
tggtactgca tcgagggagg aacatcgctt tggtggacg ccatggagaa aacccttgtc     960
cacaaggtac agaacaacaa gagagttgat gccatttcca ttgacttgga cgctccagat    1020 gatgcaaca tgtcggtcag gataggcgga aaggaacact ccggatatag caccgtcttc    1080
aacaccaccg ctctgggctg ccttgaccgc atggatctgc gtggtctcaa cttgcaccct    1140
acgcaagcgg atgccattcg atgtttgcat tatgacaact cgacaaaggt agctctcaag    1200
tttagctacc cgtggtggat caaggactgt ggcatcactt gcggtggcgc ggcctcgact    1260
gatctgcctc tacgaacttg cgtataccca tcctacaact tggccgatac tggtgaggct    1320
gttctgcttg cctcatacac ttggtctcag gacgcaactc gcattggatc gttggtgaag    1380
gaagctccac cacagccgcc caaggaagat gagctcgtcg agctgatcct gcagaacctg    1440
gcccgcctgc acgctgagca tatgacttat gagaagatta aggaggctta cacggcgta     1500 tatcacgcct attgctgggc taatgatccc aatgtcggtg gcgctttcgc cctcttcggt    1560
cccggccagt tcagcaatct gtatccgtac ctgatgcgac cagcggcggg cggcaagttc    1620
catatcgtcg gagaggcatc tagcgtacat cacgcctgga tcataggtc tttggagagt    1680 gcttacaccg ctgtttacca gttccgatac aagtacaaga tgtgggatta cttaaagctg    1740
ttgttggagc gctggcagta tggtctccag gagttagaga cggggaagca cggtacggct    1800
catttgcagt ttattctggg ttcacttccc aaggagtacc aggtgaagat ctaa          1854
```

-continued

```
<210> SEQ ID NO: 2
<211> LENGTH: 617
<212> TYPE: PRT
<213> ORGANISM: Trichoderma harzianum

<400> SEQUENCE: 2

Met Asp Asn Val Asp Phe Ala Glu Ser Val Arg Thr Arg Trp Ala Arg
  1               5                  10                  15

Arg Leu Ile Arg Glu Lys Val Ala Lys Glu Leu Asn Ile Leu Thr Glu
                 20                  25                  30

Arg Leu Gly Glu Val Pro Gly Ile Pro Pro Asn Glu Gly Arg Phe
             35                  40                  45

Leu Gly Gly Gly Tyr Ser His Asp Asn Leu Pro Ser Asp Pro Leu Tyr
         50                  55                  60

Ser Ser Ile Lys Pro Ala Leu Leu Lys Glu Ala Pro Arg Ala Glu Glu
 65                  70                  75                  80

Glu Leu Pro Pro Arg Lys Val Cys Ile Val Gly Ala Gly Val Ser Gly
                 85                  90                  95

Leu Tyr Ile Ala Met Ile Leu Asp Asp Leu Lys Ile Pro Asn Leu Thr
            100                 105                 110

Tyr Asp Ile Phe Glu Ser Ser Ser Arg Thr Gly Gly Arg Leu Tyr Thr
            115                 120                 125

His His Phe Thr Asp Ala Lys His Asp Tyr Tyr Asp Ile Gly Ala Met
        130                 135                 140

Arg Tyr Pro Asp Ile Pro Ser Met Lys Arg Thr Phe Asn Leu Phe Lys
145                 150                 155                 160

Arg Thr Lys Met Pro Leu Ile Lys Tyr Tyr Leu Asp Gly Glu Asn Thr
                165                 170                 175

Pro Gln Leu Tyr Asn Asn His Phe Phe Ala Lys Gly Val Ser Asp Pro
            180                 185                 190

Tyr Met Val Ser Val Ala Asn Gly Gly Thr Val Pro Asp Asp Val Val
            195                 200                 205

Asp Ser Val Gly Glu Lys Leu Gln Gln Ala Phe Gly Tyr Tyr Lys Glu
        210                 215                 220

Lys Leu Ala Glu Asp Phe Asp Lys Gly Phe Asp Glu Leu Met Leu Val
225                 230                 235                 240

Asp Asp Met Thr Thr Arg Glu Tyr Leu Lys Arg Gly Gly Pro Lys Gly
                245                 250                 255

Glu Ala Pro Lys Tyr Asp Phe Ala Ile Gln Trp Met Glu Thr Gln
            260                 265                 270

Asn Thr Gly Thr Asn Leu Phe Asp Gln Ala Phe Ser Glu Ser Val Ile
            275                 280                 285

Asp Ser Phe Asp Phe Asp Asn Pro Thr Lys Pro Glu Trp Tyr Cys Ile
        290                 295                 300

Glu Gly Gly Thr Ser Leu Leu Val Asp Ala Met Glu Lys Thr Leu Val
305                 310                 315                 320

His Lys Val Gln Asn Asn Lys Arg Val Asp Ala Ile Ser Ile Asp Leu
                325                 330                 335

Asp Ala Pro Asp Asp Gly Asn Met Ser Val Arg Ile Gly Gly Lys Glu
            340                 345                 350

His Ser Gly Tyr Ser Thr Val Phe Asn Thr Thr Ala Leu Gly Cys Leu
            355                 360                 365

Asp Arg Met Asp Leu Arg Gly Leu Asn Leu His Pro Thr Gln Ala Asp
        370                 375                 380
```

```
Ala Ile Arg Cys Leu His Tyr Asp Asn Ser Thr Lys Val Ala Leu Lys
385                 390                 395                 400

Phe Ser Tyr Pro Trp Trp Ile Lys Asp Cys Gly Ile Thr Cys Gly Gly
                405                 410                 415

Ala Ala Ser Thr Asp Leu Pro Leu Arg Thr Cys Val Tyr Pro Ser Tyr
                420                 425                 430

Asn Leu Ala Asp Thr Gly Glu Ala Val Leu Leu Ala Ser Tyr Thr Trp
            435                 440                 445

Ser Gln Asp Ala Thr Arg Ile Gly Ser Leu Val Lys Glu Ala Pro Pro
    450                 455                 460

Gln Pro Pro Lys Glu Asp Glu Leu Val Glu Leu Ile Leu Gln Asn Leu
465                 470                 475                 480

Ala Arg Leu His Ala Glu His Met Thr Tyr Glu Lys Ile Lys Glu Ala
                485                 490                 495

Tyr Thr Gly Val Tyr His Ala Tyr Cys Trp Ala Asn Asp Pro Asn Val
                500                 505                 510

Gly Gly Ala Phe Ala Leu Phe Gly Pro Gly Gln Phe Ser Asn Leu Tyr
            515                 520                 525

Pro Tyr Leu Met Arg Pro Ala Ala Gly Gly Lys Phe His Ile Val Gly
    530                 535                 540

Glu Ala Ser Ser Val His His Ala Trp Ile Ile Gly Ser Leu Glu Ser
545                 550                 555                 560

Ala Tyr Thr Ala Val Tyr Gln Phe Arg Tyr Lys Tyr Lys Met Trp Asp
                565                 570                 575

Tyr Leu Lys Leu Leu Leu Glu Arg Trp Gln Tyr Gly Leu Gln Glu Leu
            580                 585                 590

Glu Thr Gly Lys His Gly Thr Ala His Leu Gln Phe Ile Leu Gly Ser
            595                 600                 605

Leu Pro Lys Glu Tyr Gln Val Lys Ile
    610                 615

<210> SEQ ID NO: 3
<211> LENGTH: 34
<212> TYPE: PRT
<213> ORGANISM: Trichoderma harzianum

<400> SEQUENCE: 3

Glu Glu Leu Pro Pro Arg Lys Val Cys Ile Val Gly Ala Gly Val Ser
1               5                   10                  15

Gly Leu Tyr Ile Ala Met Ile Leu Asp Asp Leu Lys Ile Pro Asn Thr
            20                  25                  30

Leu Tyr

<210> SEQ ID NO: 4
<211> LENGTH: 8
<212> TYPE: PRT
<213> ORGANISM: Trichoderma harzianum

<400> SEQUENCE: 4

Phe Ser Tyr Pro Trp Trp Ile Lys
1               5

<210> SEQ ID NO: 5
<211> LENGTH: 11
<212> TYPE: PRT
<213> ORGANISM: Trichoderma harzianum
```

```
<400> SEQUENCE: 5

Tyr Tyr Leu Asp Gly Glu Asn Thr Pro Gln Leu
 1               5                  10

<210> SEQ ID NO: 6
<211> LENGTH: 11
<212> TYPE: PRT
<213> ORGANISM: Trichoderma harzianum

<400> SEQUENCE: 6

Gly Val Ser Asp Pro Tyr Met Val Ser Val Ala
 1               5                  10

<210> SEQ ID NO: 7
<211> LENGTH: 16
<212> TYPE: PRT
<213> ORGANISM: Trichoderma harzianum
<220> FEATURE:
<223> OTHER INFORMATION: Xaa = The amino acid residue was not
      determinable

<400> SEQUENCE: 7

Arg Asp Tyr Tyr Asp Ile Gly Ala Xaa Arg Tyr Pro Asp Ile Xaa Ser
 1               5                  10                  15

<210> SEQ ID NO: 8
<211> LENGTH: 7
<212> TYPE: PRT
<213> ORGANISM: Trichoderma harzianum

<400> SEQUENCE: 8

Arg Thr Phe Asn Leu Phe Lys
 1               5

<210> SEQ ID NO: 9
<211> LENGTH: 24
<212> TYPE: PRT
<213> ORGANISM: Trichoderma harzianum
<220> FEATURE:
<223> OTHER INFORMATION: Xaa = The amino acid residue was not
      determinable.

<400> SEQUENCE: 9

Tyr Val Asp Ala Ile Ser Ile Asp Leu Asp Ala Pro Asp Asp Gly Asn
 1               5                  10                  15

Xaa Ser Val Xaa Ile Gly Gly Lys
                20

<210> SEQ ID NO: 10
<211> LENGTH: 20
<212> TYPE: PRT
<213> ORGANISM: Trichoderma harzianum

<400> SEQUENCE: 10

Ala Ala Arg Gly Thr Asn Thr Gly Tyr Ala Thr His Gly Thr Asn Gly
 1               5                  10                  15

Gly Asn Gly Cys
                20

<210> SEQ ID NO: 11
<211> LENGTH: 18
<212> TYPE: PRT
<213> ORGANISM: Trichoderma harzianum
```

-continued

```
<400> SEQUENCE: 11

Tyr Thr Thr Asp Ala Thr Cys Cys Ala Cys Ala Asn Gly Gly Arg
1               5                   10                  15

Thr Ala

<210> SEQ ID NO: 12
<211> LENGTH: 695
<212> TYPE: PRT
<213> ORGANISM: Trichoderma harzianum

<400> SEQUENCE: 12

Met Lys Trp Ser Ala Arg Gly Cys Gly Thr Ala Arg Leu Pro Ala Asn
1               5                   10                  15

Ser Ala Val Thr Ala Ser Leu Pro Leu Lys Leu Glu Thr Arg Ser Ser
                20                  25                  30

Leu Asn Ser Arg Leu Ser Asn Ile His Val Glu Arg Ser Ala Ser Val
            35                  40                  45

Glu Gly Ala Leu Ser Tyr Thr Tyr Gly Ser Cys Gln Ala Lys Arg Glu
        50                  55                  60

Glu Glu Ala His His Ser Ile Ser Gln Pro Thr Asp Ala His His Asp
65                  70                  75                  80

Arg Leu Val Trp Val Ile Pro Glu Asn Val Gln Ser Gly Gly Cys Ile
                85                  90                  95

Ser Ala Trp Ser Arg Ala Asn Gly Arg Leu Val Gly Arg Ser Arg Pro
            100                 105                 110

Gln Ser Phe Asp Phe Lys Ser Ile Lys Met Arg Arg Asp Leu Lys Ala
        115                 120                 125

Arg Ala Thr Lys Pro Ser Asp Ser Val Ala Ile His Met Thr Thr Asp
    130                 135                 140

Asn Gly Ile Asn Pro Trp Gly Pro Trp Phe Asp Gly Val Lys Leu Leu
145                 150                 155                 160

Glu Asp Lys Glu Ile Ser Thr Val Asp Val Glu Lys Ala Lys Ser Lys
                165                 170                 175

Asn Ile Ala Ile Val Gly Ala Gly Met Ser Gly Leu Met Thr Tyr Leu
            180                 185                 190

Cys Leu Thr Gln Ala Gly Met Thr Asn Val Ser Ile Ile Glu Gly Gly
        195                 200                 205

Asn Arg Leu Gly Gly Arg Val His Thr Glu Tyr Leu Ser Gly Gly Pro
    210                 215                 220

Phe Asp Tyr Ser Tyr Gln Glu Met Gly Pro Met Arg Phe Pro Asn Thr
225                 230                 235                 240

Ile Thr Leu Gly Asn Glu Thr Tyr Asn Val Ser Asp His Gln Leu Val
                245                 250                 255

Phe Gln Leu Ala Glu Glu Met Asn Ser Leu Asn Gly His Ser Lys Asn
            260                 265                 270

Leu Ser Val Asp Phe Ile Pro Trp Tyr Gln Ser Asn Ser Asn Gly Leu
        275                 280                 285

Tyr Tyr Tyr Asp Gly Ile Lys Asn Pro Glu Thr Gly Leu Pro Pro Thr
    290                 295                 300

Leu Ala Glu Leu Ala Ala Asn Ser Ser Leu Ala Leu Thr Arg Val Ser
305                 310                 315                 320

Asn Asn Ser Thr Lys Ser Leu Ser Gln Lys Val Asp Ala Phe Leu Pro
                325                 330                 335
```

```
Asp Thr Asp Lys Phe Leu Ala Glu Met Ala Gln Asn Met Phe Lys Ala
            340                 345                 350

His Ala Asp Trp Leu Ser Gly Gly Leu Ala Gly Leu Pro Gly Asp Gln
            355                 360                 365

Trp Ser Glu Phe Gly Phe Met Val Asn Tyr Leu Arg Gly Ser Leu Asn
            370                 375                 380

Asp Thr Ala Phe Leu Ala Pro Ala Leu Thr Arg Thr Gly Thr Arg Cys
385                     390                 395                 400

Thr Lys Gly Cys Thr Phe Pro Arg Arg Arg Gly Ala Ile Asp Gly Gly
                    405                 410                 415

Leu Asn Arg Leu Pro Leu Ser Phe His Pro Leu Val Asp Asn Ala Thr
            420                 425                 430

Thr Leu Asn Arg Arg Leu Glu Arg Val Ala Phe Asp Ala Glu Thr Gln
            435                 440                 445

Lys Val Thr Leu His Ser Arg Asn Ser Tyr Lys Asp Ser Phe Glu Ser
            450                 455                 460

Ser Glu His Asp Tyr Ala Val Ile Ala Ala Pro Phe Ser Ile Val Lys
465                     470                 475                 480

Lys Trp Arg Phe Ser Pro Ala Leu Asp Leu Thr Ala Pro Thr Leu Ala
                    485                 490                 495

Asn Ala Ile Gln Asn Leu Glu Tyr Thr Ser Ala Cys Lys Val Ala Leu
                    500                 505                 510

Glu Phe Arg Thr Arg Phe Trp Glu His Leu Pro Gln Pro Ile Tyr Gly
                    515                 520                 525

Ser Cys Ser Thr Thr Ser Asp Ile Pro Gly Ile Gly Ser Ile Cys Tyr
            530                 535                 540

Pro Ser Tyr Asn Ile Asn Gly Thr Asp Gly Pro Ala Ser Ile Leu Ala
545                     550                 555                 560

Ser Tyr Ile Ser Gly Ala Asp Trp Gly Asp Arg Trp Val Ser Thr Pro
                    565                 570                 575

Glu Glu Glu His Val Gln Tyr Val Leu Asn Ala Met Ala Glu Ile His
            580                 585                 590

Gly Glu Glu Leu Val Lys Glu Gln Tyr Thr Gly Gln Phe Asn Arg Arg
            595                 600                 605

Cys Trp Ala Leu Asp Pro Leu Glu Ser Ala Ser Trp Ala Ser Pro Thr
            610                 615                 620

Val Gly Gln His Glu Leu Tyr Leu Pro Glu Tyr Phe Gln Thr Arg Asn
625                     630                 635                 640

Asn Leu Val Phe Val Gly Glu His Thr Ser Tyr Thr His Ala Trp Ile
                    645                 650                 655

Ala Ser Ala Leu Glu Ser Gly Ile Arg Gly Ser Val Gln Leu Leu Leu
                    660                 665                 670

Glu Leu Gly Leu Val Asp Glu Ala Lys Gly Arg Pro Val Asp Lys Trp
            675                 680                 685

Met Ala Arg Trp Ile Asp Val
            690             695
```

NUCLEIC ACIDS ENCODING POLYPEPTIDES HAVING L-AMINO ACID OXIDASE ACTIVITY

CROSS-REFERENCE TO RELATED APPLICATION

This application is a continuation-in-part of pending U.S. application Ser. No. 09/080,428 filed on May 18, 1998, now abandoned which application is fully incorporated herein by reference.

BACKGROUND OF THE INVENTION

1. Field of the Invention

The present invention relates to isolated nucleic acid sequences encoding polypeptides having L-amino acid oxidase activity. The invention also relates to nucleic acid constructs, vectors, and host cells comprising the nucleic acid sequences as well as recombinant methods for producing the polypeptides.

2. Description of the Related Art

Polypeptides having L-amino acid oxidase activity catalyze the oxidative deamination of L-amino acids to produce the corresponding 2-keto acids. Such polypeptides are classified under the Enzyme Classification Number E.C. 1.4.3.2 of the International Union of Biochemistry and Molecular Biology.

WO 94/25574 discloses an L-amino acid oxidase from *Trichoderma harzianum* which has a broad substrate specificity. JP 78115867A discloses an L-amino acid oxidase from *Trichoderma viride* which has a very high substrate specificity toward L-lysine.

Niedermann and Lerch (1990, *Journal of Biological Chemistry* 265: 17246–17251) disclose the molecular cloning of the L-amino acid oxidase gene from *Neurospora crassa*.

Bockholt et al. (1995, *Biochimica et Biophysica Acta* 1264: 289–293) disclose the cloning and DNA sequence analysis of the L-amino acid oxidase gene from the cyanobacterium Synechococcus PCC6301.

It is an object of the present invention to provide new isolated nucleic acid sequences encoding polypeptides having L-amino acid oxidase activity.

SUMMARY OF THE INVENTION

The present invention relates to isolated nucleic acid sequences encoding polypeptides having L-amino acid oxidase activity, selected from the group consisting of:

(a) a nucleic acid sequence encoding a polypeptide having an amino acid sequence which has at least 50% identity with amino acids 1 to 617 of SEQ ID NO. 2;

(b) a nucleic acid sequence having at least 50% homology with nucleotides 1 to 1851 of SEQ ID NO. 1;

(c) a nucleic acid sequence which hybridizes under low stringency conditions with (i) nucleotides 1 to 1851 of SEQ ID NO. 1, (ii) the genomic DNA sequence comprising nucleotides 1 to 1851 of SEQ ID NO. 1, (iii) a subsequence of (i) or (ii) of at least about 100 nucleotides, or (iv) a complementary strand of (i), (ii), or (iii);

(d) a nucleic acid sequence encoding a variant of the polypeptide having an amino acid sequence of SEQ ID NO. 2 comprising a substitution, deletion, and/or insertion of one or more amino acids;

(e) an allelic variant of (a), (b), or (c);

(f) a subsequence of (a), (b), (c), or (e), wherein the subsequence encodes a polypeptide fragment which has L-amino acid oxidase activity; and (g) a nucleic acid sequence encoding a polypeptide having L-amino acid oxidase activity with physicochemical properties of (i) a pH optimum in the range of from about pH 8.5 to about pH 9.5 determined after incubation for 20 minutes at 20° C. in the presence of L-arginine; (ii) a pH stability of 80% or more, relative to initial activity, at pH 9.5 determined after incubation for 1 hour at 40° C. in the absence of substrate; and (iii) an activity towards L-arginine, L-lysine, L-methionine, L-asparagine, L-phenylalanine, and/or L-leucine.

The present invention also relates to nucleic acid constructs, vectors, and host cells comprising the nucleic acid sequences as well as recombinant methods for producing the polypeptides.

BRIEF DESCRIPTION OF THE FIGURES

FIGS. 4A and 4B show the cDNA nucleic acid sequence and the deduced amino acid sequence of a Trichoderma harzianum CBS 223.93 L-amino acid oxidase gene (SEQ ID NOs. 1 and 2, respectively).

DETAILED DESCRIPTION OF THE INVENTION

Figure 1:
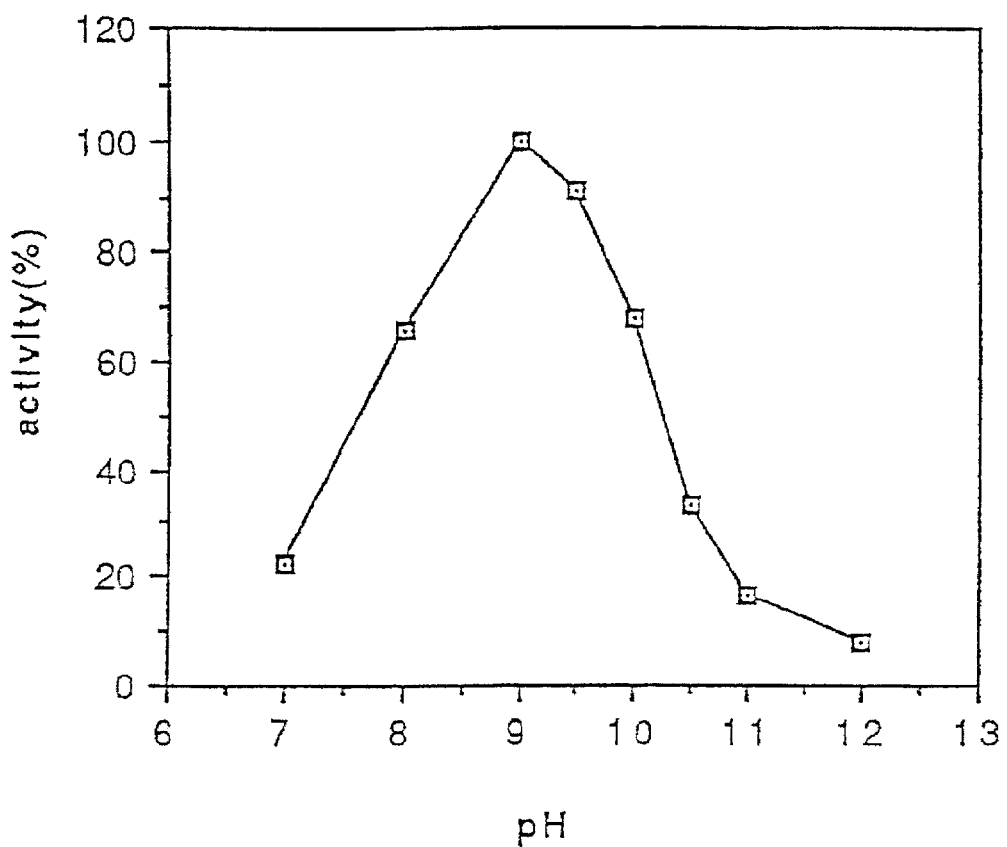
FIG. 1 shows the pH activity profile (% activity) of a *Trichoderma harzianum* CBS 223.93 L-amino acid oxidase.

Isolated Nucleic Acid Sequences Encoding Polypeptides Having L-amino Acid Oxidase Activity The term "L-amino acid oxidase activity" is defined herein as a deaminating activity which catalyzes the deamination of an L-amino acid in the presence of water and oxygen to produce a 2-oxo acid, ammonia, and hydrogen peroxide. Defined in a general manner, the L-amino acid oxidase activity may be capable of oxidizing any L-amino acid selected from the group consisting of Ala, Arg, Asn, Asp, Cys, Gln, Glu, Gly, His, Ile, Leu, Lys, Met, Phe, Pro, Ser, Thr, Trp, Tyr, and/or Val, but at least Arg, Lys, Met, Asn, Phe, and/or Leu. It will be understood that the isolated polypeptides having L-amino acid oxidase activity of the present invention may be unspecific as to the amino acid.

For purposes of the present invention, L-amino acid oxidase activity is determined according to the procedure described in WO 94/25574 where the hydrogen peroxide produced during the deamidation of L-arginine is measured by coupling the reaction to a peroxidase in the presence of 2,2'-azinobis(3-ethylbenzothiazoline-6sulfonate) (ABTS) which produces a greenish-blue color at 418 nm. One unit of L-amino acid oxidase activity is defined as 1.0 μmole of hydrogen peroxide produced per minute at 20° C. in 50 mM phosphate buffer at pH 8.5 with 1 mM L-arginine as substrate.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

In a first embodiment, the present invention relates to isolated nucleic acid sequences encoding polypeptides having an amino acid sequence which has a degree of identity to amino acids 1 to 617 of SEQ ID NO. 2 of at least about 50%, preferably at least about 55%, preferably at least about 60%, preferably at least about 65%, preferably at least about 70%, preferably at least about 75%, preferably at least about 80%, more preferably at least about 85%, even more preferably at least about 90%, most preferably at least about 95%, and even most preferably at least about 97%, which have L-amino acid oxidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 1 to 617 of SEQ ID NO. 2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the nucleic acid sequences of the present invention encode polypeptides that comprise the amino acid sequence of SEQ ID NO. 2 or an allelic variant thereof; or a fragment thereof that has L-amino acid oxidase activity. In a more preferred embodiment, the nucleic acid sequence of the present invention encodes a polypeptide that comprises the amino acid sequence of SEQ ID NO. 2. In another preferred embodiment, the nucleic acid sequence of the present invention encodes a polypeptide that comprises amino acids 1 to 617 of SEQ ID NO. 2, or an allelic variant thereof; or a fragment thereof that has L-amino acid oxidase activity. In another preferred embodiment, the nucleic acid sequence of the present invention encodes a polypeptide that comprises amino acids 1 to 617 of SEQ ID NO. 2. In another preferred embodiment, the nucleic acid sequence of the present invention encodes a polypeptide that consists of the amino acid sequence of SEQ ID NO. 2 or an allelic variant thereof; or a fragment thereof that has L-amino acid oxidase activity. In another preferred embodiment, the nucleic acid sequence of the present invention encodes a polypeptide that consists of the amino acid sequence of SEQ ID NO. 2. In another preferred embodiment, the nucleic acid sequence of the present invention encodes a polypeptide that consists of amino acids 1 to 617 of SEQ ID NO. 2 or an allelic variant thereof; or a fragment thereof that has L-amino acid oxidase activity. In another preferred embodiment, the nucleic acid sequence of the present invention encodes a polypeptide that consists of amino acids 1 to 617 of SEQ ID NO. 2.

The present invention also encompasses nucleic acid sequences which encode a polypeptide having the amino acid sequence of SEQ ID NO. 2, which differ from SEQ ID NO. 1 by virtue of the degeneracy of the genetic code. The present invention also relates to subsequences of SEQ ID NO. 1 which encode fragments of SEQ ID NO. 2 which have L-amino acid oxidase activity.

A subsequence of SEQ ID NO. 1 is a nucleic acid sequence encompassed by SEQ ID NO. 1 except that one or more nucleotides from the 5' and/or 3' end have been deleted. Preferably, a subsequence contains at least 1491 nucleotides, more preferably at least 1581 nucleotides, even more preferably at least 1671 nucleotides, and most preferably at least 1761 nucleotides. A fragment of SEQ ID NO. 2 is a polypeptide having one or more amino acids deleted from the amino and/or carboxy terminus of this amino acid sequence. Preferably, a fragment contains at least 497 amino acid residues, more preferably at least 527 amino acid residues, even more preferably at least 557 amino acids, and most preferably at least 587 amino acid residues.

An allelic variant denotes any of two or more alternative forms of a gene occupying the same chomosomal locus. Allelic variation arises naturally through mutation, and may result in polymorphism within populations. Gene mutations can be silent (no change in the encoded polypeptide) or may encode polypeptides having altered amino acid sequences. The allelic variant of a polypeptide is a polypeptide encoded by an allelic variant of a gene.

In a second embodiment, the present invention relates to isolated nucleic acid sequences which have a degree of homology to the polypeptide coding sequence of SEQ ID NO. 1 (i.e., nucleotides 1 to 1851) of at least about 50%, preferably at least about 55%, preferably at least about 60%, preferably at least about 65%, preferably at least about 70%, preferably at least about 75%, preferably at least about 80%, preferably at least about 85%, more preferably at least about 90%, even more preferably at least about 95%, and most preferably at least about 97% homology, which encode an active polypeptide; or allelic variants and subsequences of SEQ ID NO. 1 which encode polypeptide fragments which have L-amino acid oxidase activity. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=3, gap penalty=3, and windows=20.

In a third embodiment, the present invention relates to isolated nucleic acid sequences encoding polypeptides having L-amino acid oxidase activity which hybridize under very low stringency conditions, preferably low stringency conditions, more preferably medium stringency conditions, more preferably medium-bigh stringency conditions, even more preferably high stringency conditions, and most preferably very high stringency conditions with a nucleic acid probe which hybridizes under the same conditions with (i) nucleotides 1 to 1851 of SEQ ID NO. 1, (ii) the genomic DNA sequence comprising nucleotides 1 to 1851 of SEQ ID NO. 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO. 1 may be at least about 100 nucleotides or preferably at least about 200 nucleotides. Moreover, the subsequence may encode a polypeptide fragment which has L-amino acid oxidase activity.

The nucleic acid sequence of SEQ ID NO. 1 or a subsequence thereof, as well as the amino acid sequence of SEQ ID NO. 2 or a fragment thereof, may be used to design a nucleic acid probe to identify and clone DNA encoding polypeptides having L-amino acid oxidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having L-amino acid oxidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO. 1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO. 1, its complementary strand, or a subsequence thereof, under very low to very high stringency conditions. Molecules to which the nucleic acid probe hybridizes under these conditions are detected using X-ray film.

In another preferred embodiment, the nucleic acid probe is a nucleic acid sequence which encodes the polypeptide of SEQ ID NO. 2, or a subsequence thereof. In another preferred embodiment, the nucleic acid probe is SEQ ID NO. 1. In another preferred embodiment, the nucleic acid probe is nucleotides 1 to 1851 of SEQ ID NO. 1, which encodes a polypeptide having L-amino acid oxidase activity. In another preferred embodiment, the nucleic acid probe is the nucleic acid sequence contained in plasmid pEJG32 which is contained in *Escherichia coli* NRRL B-21975, wherein the nucleic acid sequence encodes a polypeptide having L-amino acid oxidase activity. In another preferred embodiment, the nucleic acid probe is the polypeptide coding region contained in plasmid pEJG32 which is contained in *Escherichia coli* NRRL B-21975.

For long probes of at least about 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least about 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The present invention also relates to isolated nucleic acid sequences produced by (a) hybridizing a DNA under very low, low, medium, medium-high, high, or very high stringency conditions with (i) nucleotides 1 to 1851 of SEQ ID NO. 1, (ii) the genomic DNA sequence comprising nucleotides 1 to 1851 of SEQ ID NO. 1, (iii) a subsequence of (i) or (ii), or (iv) a complementary strand of (i), (ii), or (iii); and (b) isolating the nucleic acid sequence. The subsequence is preferably a sequence of at least about 100 nucleotides such as a sequence which encodes a polypeptide fragment which has L-amino acid oxidase activity.

In a fourth embodiment, the present invention relates to isolated nucleic acid sequences which encode variants of the polypeptide having an amino acid sequence of SEQ ID NO. 2 comprising a substitution, deletion, and/or insertion of one or more amino acids.

The amino acid sequences of the variant polypeptides may differ from the amino acid sequence of SEQ ID NO. 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Modification of a nucleic acid sequence of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO. 1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for L-amino acid oxidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

In a fifth embodiment, the present invention relates to isolated nucleic acid sequences encoding polypeptides with L-amino acid oxidase activity having the following physicochemical properties: (a) a pH optimum in the range of from about pH 8.5 to about pH 9.5 determined after incubation for 20 minutes at 20° C. in the presence of L-arginine; (b) a pH stability of 80% or more, relative to initial activity, at pH 9.5 determined after incubation for 1 hour at 40° C. in the absence of substrate; and (c) an activity towards L-arginine, L-lysine, L-methionine, L-asparagine, L-phenylalanine, and/or L-leucine, as disclosed in WO 94/25574.

The polypeptides encoded by the isolated nucleic acid sequences of the present invention have at least 20%, preferably at least 40%, more preferably at least 60%, even more preferably at least 80%, even more preferably at least 90%, and most preferably at least 100% of the L-amino acid oxidase activity of the polypeptide of SEQ ID NO. 2.

The nucleic acid sequences of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide encoded by a nucleic acid sequence of the present invention is secreted extracellularly.

The nucleic acid sequences may be obtained from a bacterial source. For example, these polypeptides may be obtained from a gram positive bacterium such as a Bacillus strain, e.g., *Bacillus alkalophilus*, *Bacillus amyloliquefaciens*, *Bacillus brevis*, *Bacillus circulans*, *Bacillus coagulans*, *Bacillus lautus*, *Bacillus lentus*, *Bacillus licheniformis*, *Bacillus megaterium*, *Bacillus stearothermophilus*, *Bacillus subtilis*, or *Bacillus thuringiensis*; or a Streptomyces strain, e.g., *Streptomyces lividans* or *Streptomyces murinus*; or from a gram negative bacterium, e.g., *E. coli* or Pseudomonas sp.

The nucleic acid sequences may be obtained from a fungal source, and more preferably from a yeast strain such as a Candida, Hansenula, Kluyveromyces, Pichia, Saccharomyces, Schizosaccharomyces, or Yarrowia strain; or more preferably from a filamentous fungal strain such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma strain.

In a preferred embodiment, the nucleic acid sequences are obtained from a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* strain.

In another preferred embodiment, the nucleic acid sequences are obtained from an *Aspergillus aculeatus*, *Aspergillus awamori*, *Aspergillus foetidus*, *Aspergillus japonicus*, *Aspergillus nidulans*, *Aspergillus niger*, *Aspergillus oryzae*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, or *Penicillium purpurogenum*, strain.

In another preferred embodiment, the nucleic acid sequences are obtained from a *Trichoderma citrinoviride*, *Trichoderma hamatum*, *Trichoderma harzianum*, *Trichoderma koningii*, *Trichoderma longibrachiatum*, *Trichoderma polysporum*, *Trichoderma reesei*, *Trichoderma saturnisporum*, or *Trichoderma viride* strain.

In a more preferred embodiment, the nucleic acid sequences are obtained from a *Trichoderma harzianum* strain, and in a most preferred embodiment, the nucleic acid sequence is obtained from *Trichoderma harzianum* CBS 223.93, e.g., the nucleic acid sequence set forth in SEQ ID NO. 1. In another most preferred embodiment, the nucleic acid sequence is the sequence contained in plasmid pEJG32 which is contained in *Escherichia coli* NRRL B-21975.

It will be understood that for the aforementioned species, the invention encompasses both the perfect and imperfect states, and other taxonomic equivalents, e.g, anamorphs, regardless of the species name by which they are known. Those skilled in the art will readily recognize the identity of appropriate equivalents. For example, the polypeptides may be obtained from microorganisms which are taxonomic equivalents of Trichoderma as defined by D. L. Hawksworth, P. M. Kirk, B. C. Sutton, and D. N. Pegler, 1995, *Ainsworth & Bisby's Dictionary of the Fungi*, Eighth Edition, CAB International, Wallingford, United Kingdom, 1995, regardless of the species name by which they are known. For instance, the teleomorph form of Trichoderma is known as Hypocrea.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center NRRL).

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The present invention also relates to mutant nucleic acid sequences comprising at least one mutation in the polypeptide coding sequence of SEQ ID NO. 1, in which the mutant nucleic acid sequence encodes a polypeptide which consists of amino acids 1 to 617 of SEQ ID NO. 2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Trichoderma, or another or related organism and thus, for example, may be an allelic or species variant of the polypeptide encoding region of the nucleic acid sequence.

A nucleic acid sequence of the present invention may also encode fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Methods for Producing Mutant Nucleic Acid Sequences

The present invention further relates to methods for producing a mutant nucleic acid sequence, comprising introducing at least one mutation into the polypeptide coding sequence of SEQ ID NO. 1 or a subsequence thereof, wherein the mutant nucleic acid sequence encodes a polypeptide which consists of amino acids 1 to 617 of SEQ ID NO. 2 or a fragment thereof which has L-amino acid oxidase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of the genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately p laced at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrone C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of the polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of a nucleic acid sequence of the present invention that is endogenous to a cell. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the deal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli,* and pUB110, pE194, pTA1060, and pAMβ1permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g, Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide having L-amino acid oxidase activity comprising (a) cultivating a host cell under conditions suitable for production of the polypeptide; and (b) recovering the polypeptide.

The present invention also relates to methods for producing a polypeptide having L-amino acid oxidase activity comprising (a) cultivating a host cell under conditions conducive for production of the polypeptide, wherein the host cell comprises a mutant nucleic acid sequence having at least one mutation in the polypeptide coding region of SEQ ID NO. 1, wherein the mutant nucleic acid sequence encodes a polypeptide which consists of amino acids 1 to 617 of SEQ ID NO. 2, and (b) recovering the polypeptide.

The present invention further relates to methods for producing a polypeptide having L-amino acid oxidase activity comprising (a) cultivating a homologously recombinant cell, having incorporated therein a new transcription unit comprising a regulatory sequence, an exon, and/or a splice donor site operably linked to a second exon of a nucleic acid sequence of the present invention which is endogenous to a cell, under conditions suitable for production of the polypeptide encoded by the endogenous nucleic acid sequence; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* J.-C. Janson and Lars Ryden, editors, VCH Publishers, New York, 1989).

Plants

The present invention also relates to a trasgenic plant, plant part, or plant cell which has been transformed with a nucleic acid sequence encoding a polypeptide having L-amino acid oxidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol Biol.* 24: 863–878), a seed specific promoter such as the glutelin, prolamin, globulin, or albumin promoter from rice (Wu et al., 1998, *Plant and Cell Physiology* 39: 885–889), a *Vicia faba* promoter from the legumin B4 and the unknown seed protein gene from *Vicia faba* (Conrad et al, 1998, *Journal of Plant Physiology* 152: 708–711), a promoter from a seed oil body protein (Chen et al., 1998, Plant and Cell Physiology 39: 935–941), the storage protein napA promoter from *Brassica napus,* or any other seed specific promoter known in the art, e.g, as described in WO 91/14772. Furthermore, the promoter may be a leaf specific promoter such as the rbcs promoter from rice or tomato (Kyozuka et al., 1993, *Plant Physiology* 102: 991–1000), the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al, 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having L-amino acid oxidase activity of the present invention under conditions conducive for production of the polypeptide; and (b) recovering the polypeptide.

Removal or Reduction of L-Amino Acid Oxidase Activity

The present invention also relates to methods for producing a mutant cell of a parent cell, which comprises disrupting or deleting a nucleic acid sequence of the present invention or a control sequence thereof, which results in the mutant cell producing less of the polypeptide having L-amino acid oxidase activity encoded by the nucleic acid sequence than the parent cell when cultivated under the same conditions.

The construction of strains that have reduced L-amino acid oxidase activity may be conveniently accomplished by modification or inactivation of a nucleic acid sequence necessary for expression of the polypeptide having L-amino acid oxidase activity in the cell. The nucleic acid sequence to be modified or inactivated may be, for example, a nucleic acid sequence encoding the polypeptide or a part thereof essential for exhibiting L-amino acid oxidase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the L-amino acid oxidase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced L-amino acid oxidase activity or production.

Modification or inactivation of production of a polypeptide encoded by a nucleic acid sequence of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of L-amino acid oxidase activity by fermentation of a cell which produces both a polypeptide encoded by a nucleic acid sequence of the present invention as well as the protein product of interest by adding an effective amount of an agent capable of inhibiting L-amino acid oxidase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of L-amino acid oxidase activity by cultivating the cell under conditions permitting the expression of the product, subjecting the resultant culture broth to a combined pH and temperature treatment so as to reduce the L-amino acid oxidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a L-amino acid oxidase inhibitor.

In accordance with this aspect of the invention, it is possible to remove at least 60%, preferably at least 75%, more preferably at least 85%, still more preferably at least 95%, and most preferably at least 99% of the L-amino acid oxidase activity. Complete removal of L-amino acid oxidase activity may be obtained by use of this method.

The combined pH and temperature treatment is preferably carried out at a pH in the range of 9.5–10.5 and a temperature in the range of 40–60° C. for a sufficient period of time to attain the desired effect, where typically, 30 to 90 minutes is sufficient.

The methods used for cultivation and purification of the product of interest may be performed by methods known in the art.

The methods of the present invention for producing an essentially L-amino acid oxidase-free product may be of particular interest in the production of amino acids and eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The L-amino acid oxidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from L-amino acid oxidase activity which is produced by a method of the present invention.

Uses

The polypeptides having L-amino acid oxidase activity encoded by the nucleic acid sequences of the present invention may be used in a number of applications (see, e.g., WO 94/25574 and WO 97/21351).

The polypeptides having L-amino acid oxidase activity may be used in processes in which in situ generation of hydrogen peroxide is desirable. For example, the polypeptides may be advantageously incorporated into detergent compositions, in particular, detergent compositions comprising peroxidase systems, e.g., for dye transfer inhibition during laundering or for improved bleaching in laundry detergents. The polypeptides may also be incorporated into toothpaste, or used for preservation of cosmetics. The polypeptides may be used in bread and dough improving compositions.

The polypeptides may be further implemented in processes for treatment of wastewater from pulp production, and lignin modification, e.g., in particular particle board production.

The present invention is further described by the following examples which should not be construed as limiting the scope of the invention.

EXAMPLES

Chemicals used as buffers and substrates were commercial products of at least reagent grade.

Example 1

Production of *Trichoderma harzianum* CBS 223.93 L-amino Acid Oxidase

A seed culture was propagated in a 500 ml baffled shake flask containing 250 ml of a medium composed of 2.4% of corn steep liquor, 2.4% of glucose, and 0.4% of $CaCO_3$. After sterilization the medium was inoculated with mycelium from an agar slant culture of the strain *Trichoderma harzianum* A611 (CBS 223.93). The shake flask was then incubated for about 70 hours at 26° C. with shaking.

Inoculum from this seed culture was inoculated into a 2 liter fermentor having a sterile air source and impeller agitation means. The fermentor contained 1.2 liters of a medium composed of 10% of corn steep liquor, 0.5% of glucose, 0.5% of $(NH_4)_2SO_4$, 0.07% of $KH_2PO_4$, 0.2% of L-arginine and 1.0% of $CaCO_3$. The fermentor with the medium was autoclaved for 60 minutes at 120° C.

After inoculation the temperature of the medium was maintained at 28° C. and aerated at an aeration rate of 0.8 volume of air/volume of medium/minute during fermentation. The impeller speed was 900 rpm. During the first 24 hours, the pH of the fermentation medium was maintained at 6.0 by titration with a solution of 25% glucose-2.5% $H_3PO_4$. From 24 hours the pH setpoint was changed and maintained at 5.8 during the fermentation. The fermentation was allowed to proceed for about 96 hours. At this time a yield of approximately 250 mg of enzyme protein per liter was obtained.

Example 2

Purification of *Trichoderma harzianum* CBS 223.93 L-amino Acid Oxidase

A 2.7 liter volume of culture broth obtained according to Example 1 was adjusted to pH 5.0 and non-soluble material removed by filtration. The L-amino acid oxidase was adsorbed to approximately 270 g of solid $Ca_3(PO_4)_2$ suspended in one liter of 50 mM acetate pH 5.0 buffer. After stirring for 2 hours at room temperature, the slurry was filtered and adsorbed protein eluted with approximately 750 ml of 0.1 M sodium phosphate at pH 8.0. The buffer of the eluate was changed to 20 mM sodium phosphate pH 7 by ultrafiltration. Finally, the eluate was concentrated to 120 ml using a membrane with a cut off of 10,000 Da.

This sample was loaded onto a Q Sepharose Fast Flow column pre-equilibrated in 20 mM sodium phosphate pH 7.0. The column was washed with 2 column volumes of the same buffer and eluted with a gradient from 0 to 1 M NaCl in 20 mM sodium phosphate pH 7.0. Fractions containing L-amino acid oxidase activity were pooled. The pooled protein was pure as judged by SDS-PAGE.

The specific activity of the purified L-amino acid oxidase was 16 U/mg determined in a 50 mM phosphate buffer at pH 8.5, 20° C. with 1 mM L-arginine as substrate. One unit of enzyme will form 1 μmole of hydrogen peroxide per minute. The amount of protein was quantified assuming that a solution of the L-amino acid oxidase having an optical density of 1 determined at 280 nm contains 1 mg of protein/ml. The L-amino acid oxidase yield was approximately 50 mg of pure protein per liter of culture medium.

Example 3

Characterization of *Trichoderma harzianum* CBS 223.93 L-amino Acid Oxidase

Characterization of the L-amino acid oxidase obtained according to the previous examples was carried out using microtiter plates. The microtiter plates were incubated at the temperature and time intervals indicated below.

Peroxidase activity was expressed in peroxidase units (PODU), one unit being defined as the amount of enzyme which, under standard conditions (i.e., pH 7.0; temperature 30° C.; reaction time 3 minutes) catalyses the conversion of 1 μmole of hydrogen peroxide per minute. The activity was determined using an assay based on 2,2'-azinobis(3-ethylbenzothiazoline-6-sulfonate) (ABTS) as the chromophore, the greenish-blue color produced being determined by absorbance at 418 nm.

In the following characterization experiments, detection of $H_2O_2$ was carried out using a *Coprinus cinereus* peroxidase (CiP), obtained according to WO 92/16634, at a level of 4.5 PODU/ml, and 0.4 mM ABTS in phosphate buffer at pH 7.0. The hydrogen peroxide concentrations were determined relative to a freshly prepared hydrogen peroxide standard solution.

For determination of the pH optimum, the assay was carried out in two steps. In the first step, the L-amino acid oxidase was incubated for 20 minutes with 1 mM of L-arginine in 100 mM of phosphate buffer at various pH values. In the second step, the generated hydrogen peroxide was detected as described above.

The results are presented in FIG. 1. As determined by this test, the L-amino acid oxidase showed activity in the interval of from pH below 7 to a pH of approximately 12. The enzyme has a pH optimum in the range of from pH 8 to 10, more specifically in the range of from pH 8.5 to 9.5, around pH 9.

For determination of pH stability, the L-amino acid oxidase was incubated at various pH values for 1 hour at 40° C. in 50 mM of phosphate buffer. After dilution, residual activity was measured using the two-step procedure described above.

Figure 2:
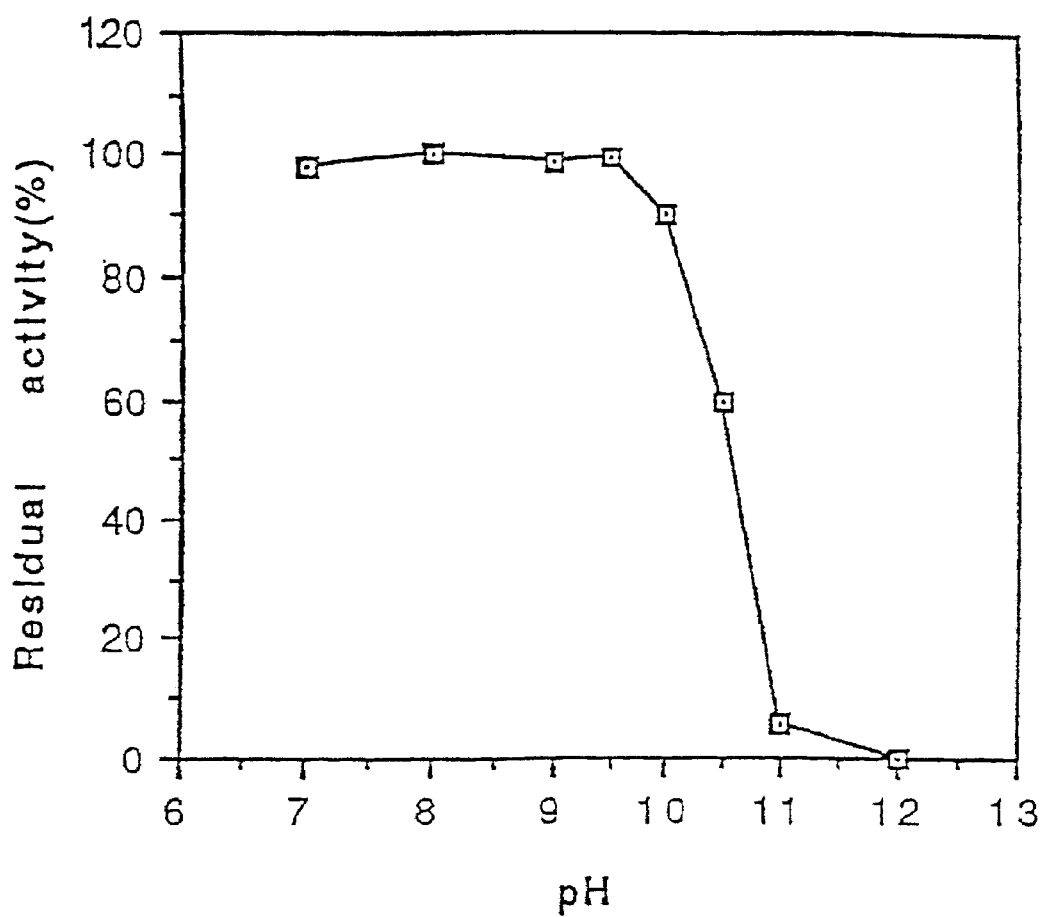
FIG. 2 shows the pH stability (% residual activity) of a *Trichoderma harzianum* CBS 223.93 L-amino acid oxidase.

The results are presented in FIG. 2. As determined by this test, the L-amino acid oxidase had a pH stability of more than 80% relative to initial activity in the range pH 7–9.5. At pH 10, the L-amino acid oxidase had a pH stability of more than 70% relative to initial activity, preferably more than 80% relative to initial activity.

For determination of temperature stability, the L-amino acid oxidase was incubated in phosphate buffer at pH 8.5 for 1 hour at various temperatures. After dilution, residual activity was measured using the two-step procedure described above.

Figure 3:
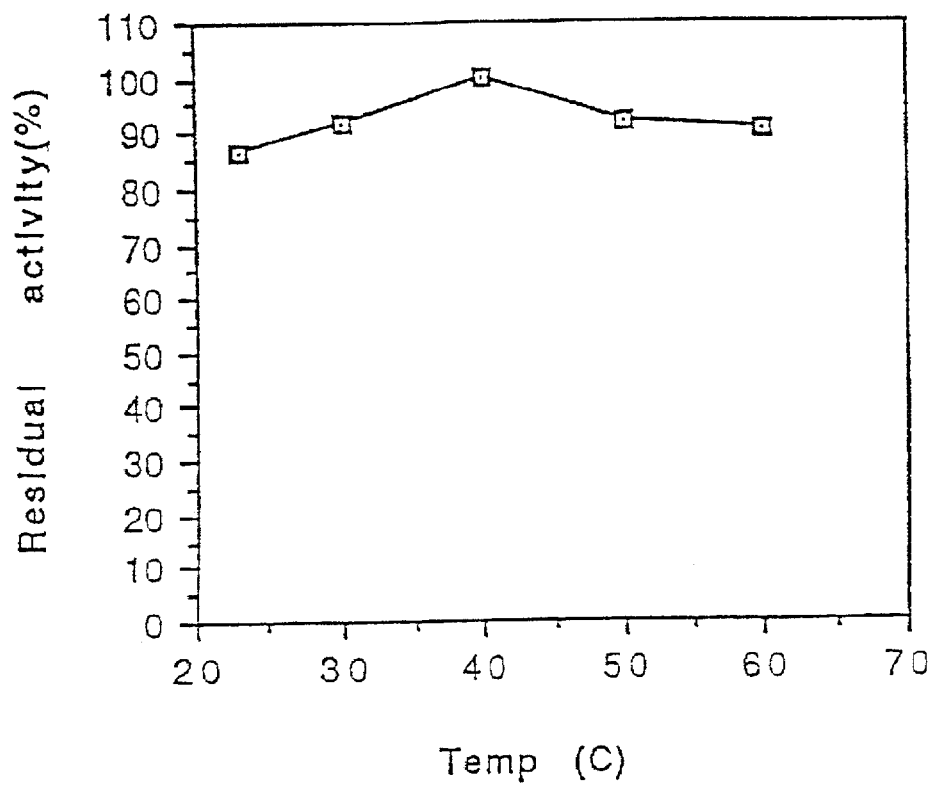
FIG. 3 shows the temperature stability (% residual activity) of a *Trichoderma harzianum* CBS 223.93 L-amino acid oxidase.

The results are presented in FIG. 3. As determined by this test, the L-amino acid oxidase was stable in the temperature range of from below 22° C. to above 60° C. The enzyme showed a temperature stability of more than 80% relative to initial activity in the range of from 25° C. to 60° C.

For determination of substrate specificity, the activity of the L-amino acid oxidase was determined with various L-amino acids as substrates. The L-amino acid oxidase was incubated with the substrate in phosphate buffer at pH 8.5 and room temperature for 20 minutes. Generated hydrogen peroxide was detected using ABTS and CiP as described above. The specific activity was determined as described in Example 2 above.

$K_m$ values for the various substrates were determined by plotting values of 1/v versus 1/s (Lineweaver-Burk plots). The results are presented in Table 1.

TABLE 1

Substrate Specificity

| Substrate | Substrate Conc. (mM) | Specific Activity (U/mg) | $K_m$ (mM) |
|---|---|---|---|
| L-leucine | 80 | 16 | 40 |
| L-phenylalamine | 80 | 25 | 25 |
| L-methionine | 80 | 8 | 15 |
| L-arginine | 10 | 30 | 1.2 |
| L-arginine | 1 | 16 | — |
| L-lysine | 1 | 7 | 0.2 |
| L-asparagine | 80 | 7 | 20 |

The L-amino acid oxidase showed activity towards L-arginine, L-lysine, L-methionine, L-asparagine, L-phenylalanine, and L-leucine. L-arginine and L-lysine had the lowest $K_m$ values, and were expected to be preferred substrates with respect to high specific activity at low substrate concentration, as also evidenced from the specific activity shown in Table 1. From these experiments the preferred substrate appeared to be L-arginine.

Example 4

Amino Acid Sequencing of *Trichoderma harzianum* CBS 223.93 L-amino Acid Oxidase The purified *Trichoderma harzianum* CBS 223.93 L-amino acid oxidase was electrophoresed and subsequently blot-transferred to a PSQ membrane (Millipore, Bedford, Mass.) using 10 mM CAPS (3-[cyclohexylamino]-1-propanesulfonic acid) pH 11 in 10% methanol for 2 hours. The PSQ membrane was stained with 0.1% Coommassie Blue R-250 in 40% methanol/1% acetic acid for 20 seconds and destained in 50% ethanol to observe the protein bands. One component at 55 kDa was excised and subjected to amino terminal sequencing on an Applied Biosystems Model 473A protein sequencer (Applied Biosystems, Inc., Foster City, Calif.) using a blot cartridge and liquid phase TFA delivery according to the manufacturer's instructions. The component yielded the following amino terminal sequence: EELPPRKVCIVGAGVSGLYIAMILD-DLKIPNTLY (SEQ ID NO. 3).

A 500 μl sample of the enzyme was dried in a Speed Vac and then reconstituted in 300 μl of 6 M guanidinium hydrochloride, 0.3 M Tris pH 8.3. The enzyme was incubated overnight and then 10 μl of 0.1 M dithiothreitol was added and incubated for 4 hours. A 40 μl volume of 0.1 M iodoacetic acid was then added and the solution was incubated for an additional hour. The reduced and alkylated enzyme was desalted on a Nap-5 column (Pharmacia, Uppsala, Sweden) in 50 mM $NH_4HCO_3$. The sample was concentrated to 150 μl (Speed Vac) and added 10 μg of lysyl endopeptidase (Wako Pure Chemicals, Ltd.) was then added. The digestion was continued overnight at 37° C.

Peptides were separated by RP-HPLC on a Vydac RP-18 column (Vydac, Hesperia, Calif.) using TFA/acetonitrile, repurified in TFA/isopropanol, and subjected to amino terminal sequencing. The following sequences were obtained from six selected peptides where X indicates the amino acid residue was not determinable: FSYPWWIK (SEQ ID NO. 4), YYLDGENTPQL (SEQ ID NO. 5), GVSDPYMVSVA (SEQ ID NO. 6), (R)DYYDIGAXRYPDIXS (SEQ ID NO. 7), RTFNLFK (SEQ ID NO. 8), and YVDAISIDLDAP-DDGNXSVXIGGK (SEQ ID NO. 9).

Example 5
RNA Isolation

*Trichoderma harzianum* CBS 223.93 was cultivated in a fermentation tank in a medium composed of 7.5 g of potato starch, 10 g of soy bean meal, 2 g of $KH_2PO_4$, 5 g of $Na_2HPO_4.2H_2O$, and 0.1 g of $ZnSO_4.7H_2O$ per liter. A two liter sample was taken after five days of growth at 30° C., and the mycelia were collected, frozen in liquid $N_2$, and stored at –80° C. Total RNA was prepared from the frozen, powdered mycelia of *Trichoderma harzianum* by extraction with guanidinium tiocyanate followed by ultracentrifugation through a 5.7 M cesium chloride cushion (Chirgwin et al., 1979, *Biochemistry* 18: 5294–5299). Poly(A)+ RNA was isolated by oligo(dT)-cellulose affinity chromatography according to the procedure of Aviv and Leder (1972, *Proceedings of the National Academy of Sciences USA* 69: 1408–1412).

Example 6
Construction of a cDNA Library

Double-stranded cDNA was synthesized from 5 μg of *Trichoderma harzianum* CBS 223.93 poly(A)+ RNA of Example 5 using the procedure described by Gubler and Hoffman (1983, *Gene* 25: 263–269) and Sambrook et al. (1989, supra), except that an oligo(dT)-NotI anchor primer, instead of an oligo(dT)12–18 primer, was used in the first strand reaction. After synthesis, the cDNA was treated with Mung bean nuclease (Life Technologies, Gaithersburg, Md.), blunt-ended with T4 DNA polymerase (Boehringer Mannheim, Indianapolis, Ind.), and ligated to non-palindromic BstXI adaptors (Invitrogen, San Diego, Calif.), using about 50-fold molar excess of the adaptors. The adapted cDNA was digested with NotI, size-fractionated for 1.2–3.0 kb cDNAs by agarose gel electrophoresis, and ligated into pYES2.0 (Invitrogen, San Diego, Calif.) cleaved with BstXI/NotI. The ligation mixture was transformed into electrocompetent *E. coli* DH10B cells (Life Technologies, Gaithersburg, Md.) according to the manufacturer's instructions. The library consisting of $1 \times 10^6$ independent clones was stored as individual pools (25,000–30,000 colony forming units/pool) in 20% glycerol at –80° C., and as double stranded cDNA and ligation mixture at –20° C. Plasmid DNA was purified from four pools using a Qiagen Plasmid Maxi Kit (Qiagen, Chatsworth, Calif.) according to the manufacturer's instructions and then was amplified in SURE cells (Stratagene, La Jolla, Calif.), creating a total of $2 \times 10^6$ colony forming units that were pooled and stored in 20% glycerol at –80° C. The titer of the pooled frozen library was $2 \times 10^7$/μl.

Example 7
Genomic DNA Extraction

*Trichoderma harzianum* CBS 223.93 was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg per ml and the mixture was then incubated at 37° C. for 30 minutes. Proteinase K (200 μg/ml) was added and the tube was incubated an additional one hour at 37° C. Finally, the sample was extracted twice with phenol:chloroform:isoamyl alcohol and the DNA precipitated with ethanol. The precipitated DNA was washed with 70% ethanol, dried under vacuum, resuspended in TE buffer, and stored at 4° C.

Example 8
PCR Amplification of *Trichoderma harzianum* CBS 223.93 L-amino Acid Oxidase Gene Based on the amino acid sequences of the *Trichoderma harzianum* CBS 223.93 partial peptides described in Example 4, the degenerate oligonucleotide primers shown below were synthesized with an Applied Biosystems Model 394 DNA/RNA Synthesizer, according to the manufacturer's instructions, for use to PCR amplify L-amino acid oxidase gene fragments from the *Aspergillus oryzae* 1568 genomic DNA described in Example 7.

Forward primer: 5'-AARGTITGYATHGTIGGIGC-3' (SEQ ID NO. 10)
Reverse primer: 5'-YTTDATCCACCANGGRTA-3' (SEQ ID NO. 11)

(R=A or G, Y=C or T, N=G or A or C or T, H=A or C or T, I=Inosine)

Amplification reactions (50 μl) were prepared using approximately 1 μl of *Trichoderma harzianum* genomic DNA, prepared as described in Example 7, as the template. Each reaction contained the following components: 1 μl of genomic DNA, 50 pmol of the forward primer, 50 pmol of the reverse primer, 200 μM each of dATP, dCTP, dGTP, and dTTP, 1×Taq DNA polymerase buffer (Invitrogen, San Diego, Calif.), and 2.5 Units of Taq DNA polymerase (Perkin-Elmer Corp., Branchburg, N.J.). The reactions were incubated in a Perkin-Elmer Model 480 Thermal Cycler programmed as follows: Cycle 1 at 94° C. for 2.5 minutes and 72° C. for 2.5 minutes; cycles 2–26 each at 94° C. for 45 seconds, 50° C. for 45 seconds, and 72° C. for 2 minutes; and cycle 27 at 94° C. for 45 seconds, 50° C. for 45 seconds, and 72° C. for 10 minutes.

The reaction products were isolated on a 1% agarose gel (Eastman Kodak, Rochester, N.Y.) where a 1 kb product band was excised from the gel and purified using Qiaex II (Qiagen, Chatsworth, Calif.) according to the manufacturer's instructions. The purified PCR product was subsequently cloned into a TOPO pCRII vector (Invitrogen, San Diego, Calif.) and the DNA sequence was determined using lac forward and reverse primers (New England BioLabs, Beverly, Mass.) using an Applied Biosystems Model 377 Automated DNA Sequencer (Applied Biosystems, Inc., Foster City, Calif.) according to the manufacturer's instructions.

The L-amino acid oxidase gene segment (1 kb) consisting of 333 codons was amplified from *Trichoderma harzianum* with the L-amino acid oxidase-specific PCR primers described above. DNA sequence analysis showed that the amplified gene segment encoded a portion of the corresponding *Trichoderma harzianum* L-amino acid oxidase gene. The L-amino acid oxidase gene segment was used to probe a *Trichoderma harzianum* cDNA library described in Example 6.

Example 9
Identification of L-amino Acid Oxidase Clones

The *Trichoderma harzianum* CBS 223.93 cDNA library described in Example 6 was plated on Luria plus 50 μg/ml carbenicillin agar plates. Colony lifts (Maniatis et al., 1982, *Molecular Cloning, A Laboratory Manual*, Cold Spring Harbor Press, Cold Spring Harbor, N.Y.) were performed on approximately 10,000 colonies and the DNA was crosslinked onto membranes (Hybond N+, Amersham, Arlington Heights, Ill.) using a UV Stratalinker (Stratagene, La Jolla, Calif.). The membranes were soaked for three hours at 45° C. in a hybridization solution containing 5×SSPE, 0.3% SDS, 50% formamide, and 10 μg/ml of denatured and sheared herring sperm DNA. The L-amino acid oxidase gene fragment isolated from *Trichoderma harzianum* as described in Example 8 was radiolabeled using the Prime IT II Labeling Kit (Stratagene, La Jolla, Calif.), denatured by adding NaOH to a final concentration of 0.1 M, and added to the hybridization solution at an activity of approximately $1\times10^6$ cpm per ml of hybridization solution. The mixture was incubated overnight at 45° C. in a shaking water bath. Following incubation, the membranes were washed two times in 2×SSC, 0.2% SDS at 55° C. and once in 2×SSC, 0.2% SDS at 65° C. The membranes were then dried on blotting paper for 15 minutes, wrapped in SaranWrap™, and exposed to X-ray film for 2 hours at −70° C. with intensifing screens (Kodak, Rochester, N.Y.).

Eleven colonies, produced strong hybridization signals with the probe. The colonies were inoculated into five ml of LB medium supplemented with 50 μg of carbenicillin per ml and grown overnight at 37° C. Miniprep DNA was prepared from each of these clones using the Wizard 373 DNA Purification Kit (Promega, Madison, Wis.). Six clones contained L-amino acid oxidase encoding sequence, as confined by DNA sequencing, and one transformant (pEJG32) was fill length. The *E. coli* transformant containing the pEJG28 plasmid was isolated and plasmid DNA was prepared using a Wizard Maxi Prep Kit (Promega, Madison, Wis.) according to the manufacturer's instructions. The plasmid DNA was transformed into *E. coli* DH5α (Gibco-BRL, Gaithersburg, Md.) and the clone was designated *E. coli* DH5α-EJG32.

Example 10
DNA Sequence Analysis of the *Trichoderma harzianum* CBS 223.93 L-amino Acid Oxidase Gene DNA sequencing of the cDNA sequence of the L-amino acid oxidase gene contained in pEJG32 in *E. coli* DH5a EJG32 described in Example 9 was performed with an Applied Biosystems Model 377 Automated DNA Sequencer on both strands using the primer walking technique with dye-terminator chemistry (Giesecke et al., 1992, *Journal of Virology Methods* 38: 47–60). Oligonucleotide sequencing primers were designed to complementary sequences in the L-amino acid oxidase gene and were synthesized on an Applied Biosystems Model 394 DNA/RNA Synthesizer according to the manufacturer's instructions.

The nucleotide sequence of the gene encoding the *Trichoderma harzianum* L-amino acid oxidase and the deduced amino acid sequence thereof is shown in FIG. 4 (SEQ ID NOs. 1 and 2, respectively). Sequence analysis of the cloned insert revealed a large open reading frame of 1851 nucleotides (excluding the stop codon) encoding a protein of 617 amino acids sequence (SEQ ID NO. 2). The G+C content of this open reading frame is 52%. Based on the rules of van Heijne (van Heijne, 1984, *Journal of Molecular Biology* 173: 243–251), there appears to be no secretory signal peptide, but the last three amino acids may be a peroxisomal targeting signal (Gonzalez, 1991, *European Journal of Biochemistry* 199: 211–215) (double underlined in FIG. 1).

The amino acid sequences of the partial peptides derived from the purified L-amino acid oxidase described in Example 4 were consistent with those found in the deduced amino acid sequence (SEQ ID NO. 2) of the *Trichoderma harzianum* L-amino acid oxidase cDNA.

The deduced amino acid sequence of the *Trichoderma harzianum* L-amino acid oxidase was compared to that of the *Neurospora crassa* L-amino acid oxidase by the Clustal method (Higgins, 1989, supra) using the LASERGENE™ MEGALIGN™ software with an identity table and the following multiple alignment parameters: Gap penalty of 10 and gap length penalty of 10. Pairwise alignment parameters were Ktuple=1, gap penalty=3, windows=5, and diagonals=5. The deduced amino acid sequence of the *Trichoderma harzianum* L-amino acid oxidase was 13.4% identical to the deduced amino acid sequence of the *Neurospora crassa* L-amino acid oxidase (SEQ ID NO. 12).

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| *E. coli* DH5α pEJG32 | NRRL B-21975 | April 13, 1998 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Various references are cited herein, the disclosures of which are incorporated by reference in their entireties.

What is claimed is:

1. An isolated nucleic acid sequence encoding a polypeptide having L-amino acid oxidase activity, selected from the group consisting of:

(a) a nucleic acid sequence encoding a polypeptide having an amino acid sequence of amino acids 1 to 617 of SEQ ID NO. 2;

(b) a nucleic acid sequence comprising nucleotides 1 to 1851 of SEQ ID NO. 1; and (c) a fragment of (a) or (b) encoding a polypeptide having L-amino acid oxidase activity.

2. The nucleic acid sequence of claim 1, which encodes a polypeptide comprising amino acids 1 to 617 of SEQ ID NO. 2.

3. The nucleic acid sequence of claim 1, which encodes a polypeptide consisting of amino acids 1 to 617 of SEQ ID NO. 2, or a fragment thereof which has L-amino acid oxidase activity.

4. The nucleic acid sequence of claim 3, which encodes a polypeptide consisting of amino acids 1 to 617 of SEQ ID NO. 2.

5. The nucleic acid sequence of claim 1, which has the nucleic acid sequence of nucleotides 1 to 1851 of SEQ ID NO. 1.

6. The nucleic acid sequence of claim 1, which is contained in the plasmid pEJG32 which is contained in *Escherichia coli* NRRL B-21975.

7. A nucleic acid construct comprising the nucleic acid sequence of claim 1 operably linked to one or more control sequences which direct the production of the polypeptide in a suitable expression host.

8. A recombinant expression vector comprising the nucleic acid construct of claim 7.

9. A recombinant host cell comprising the nucleic acid construct of claim 7.

10. A method for producing a polypeptide having L-amino acid oxidase activity comprising (a) cultivating the host cell of claim 9 under conditions suitable for production of the polypeptide; and (b) recovering the polypeptide.

* * * * *